United States Patent
Lygin et al.

(10) Patent No.: US 11,919,846 B2
(45) Date of Patent: Mar. 5, 2024

(54) CONTINUOUS PROCESS FOR PREPARING METHACROLEIN

(71) Applicant: Röhm GmbH, Darmstadt (DE)

(72) Inventors: Alexander Lygin, Griesheim (DE); Steffen Krill, Muehltal (DE); Matthias Grömping, Darmstadt (DE); Torsten Balduf, Pfungstadt (DE); Rudolf Burghardt, Darmstadt (DE)

(73) Assignee: Röhm GmbH, Darmstadt (DE)

( * ) Notice: Subject to any disclaimer, the term of this patent is extended or adjusted under 35 U.S.C. 154(b) by 533 days.

(21) Appl. No.: 17/269,648

(22) PCT Filed: Aug. 1, 2019

(86) PCT No.: PCT/EP2019/070784
§ 371 (c)(1),
(2) Date: Feb. 19, 2021

(87) PCT Pub. No.: WO2020/038696
PCT Pub. Date: Feb. 27, 2020

(65) Prior Publication Data
US 2021/0363089 A1    Nov. 25, 2021

(30) Foreign Application Priority Data

Aug. 21, 2018 (EP) .................................. 18189862

(51) Int. Cl.
*C07C 45/75* (2006.01)
*C07C 45/82* (2006.01)
*C09K 15/08* (2006.01)
*C07C 47/22* (2006.01)

(52) U.S. Cl.
CPC .............. *C07C 45/75* (2013.01); *C07C 45/82* (2013.01); *C09K 15/08* (2013.01); *C07C 47/22* (2013.01)

(58) Field of Classification Search
CPC ......... C07C 45/75; C07C 45/82; C07C 47/22; C09K 15/08
See application file for complete search history.

(56) References Cited

U.S. PATENT DOCUMENTS

| | | | |
|---|---|---|---|
| 2,848,499 A | 8/1958 | MacLean et al. | |
| 3,878,250 A | 4/1975 | Sato et al. | |
| 4,496,770 A | 1/1985 | Duembgen et al. | |
| 9,580,374 B2 | 2/2017 | Krill et al. | |
| 9,611,204 B2 | 4/2017 | Burghardt et al. | |
| 9,816,703 B2 | 11/2017 | Krill et al. | |
| 9,994,507 B2 | 6/2018 | Burghardt et al. | |
| 10,125,077 B2 | 11/2018 | Krill et al. | |
| 2016/0200660 A1* | 7/2016 | Krill | C07C 67/39 560/208 |
| 2016/0229779 A1* | 8/2016 | Hoy, IV | C07C 67/44 |

FOREIGN PATENT DOCUMENTS

| | | | |
|---|---|---|---|
| JP | 2015-44775 | 3/2015 | |
| JP | 2015044775 | * 3/2015 | ............. C07C 45/75 |
| WO | 2015/065610 | 5/2015 | |

OTHER PUBLICATIONS

Krill et al., U.S. Appl. No. 18/006,958, filed Jan. 26, 2023.
U.S. Appl. No. 18/006,958, filed Jan. 26, 2023, Krill et al.
International Search Report dated Aug. 19, 2019 in PCT/EP2019/070784.
Written Opinion dated Aug. 19, 2019 in PCT/EP2019/070784.

* cited by examiner

*Primary Examiner* — Yate' K Cutliff
(74) *Attorney, Agent, or Firm* — Grüneberg and Myers PLLC

(57) ABSTRACT

Methacrolein is prepared in a continuous process by a Mannich condensation reaction of formaldehyde with propanal. A methacrolein polymerization inhibitor is introduced during the production process and a part thereof is recycled back into the reactor where the Mannich condensation reaction is carried out.

17 Claims, No Drawings

CONTINUOUS PROCESS FOR PREPARING METHACROLEIN

CROSS-REFERENCE TO RELATED APPLICATIONS

This application is the National Stage entry under § 371 of International Application No. PCT/EP2019/070784, filed on Aug. 1, 2019, and which claims the benefit of European Application No, 18189862.8, filed on Aug. 21, 2018. The content of each of these applications is hereby incorporated by referen.ce in its entirety.

BACKGROUND OF THE INVENTION

Technical Field of the Invention

The present invention relates to methacrolein and more particularly to a continuous production process for preparing methacrolein by reacting formaldehyde with propanal.

Description of Related Art

Methacrolein, or methacrylaldehyde, is an unsaturated aldehyde. Industrially, methacrolein is a compound which is valuable as a starting material in the chemical industry, and in particular in the manufacture of polymers and synthetic resins.

Many processes for preparing methacrolein are known to the person skilled in the art and are subject-matter of relevant overview articles, as for example in the publication *Ullmann's Encyclopedia of Industrial Chemistry* 2012, Wiley-VCH Verlag GmbH & Co. KGaA, Weinheim, *Acrolein and Methacrolein*, DOI: 10.1002/14356007.a01_149.pub2.

In particular, methacrolein can be prepared by reacting formaldehyde with propanel by a Mannich condensation reaction as described in the following publications U.S. Pat. No. 7,141,702; DE 32 13 681 A1; U.S. Pat. Nos. 4,408,079; 2,848,499; JP 4173757A (JP 19900300135); JP 306942062 and EP 0 317 909 A2.

Besides, it is of special interest to execute this reaction continuously. However, one of the major technical problems in the continuous production of methacrolein is that, as many other aldehydes, methacrolein is frequently involved in self-condensation or polymerization reactions, which complicates drastically the processes for preparing methacrolein on a large scale. Indeed, methacrolein is an extremely unstable compound which is likely to easily undergo a polymerisation reaction with ease.

As pointed out in U.S. Pat. No. 3,878,250B1, when methacrolein is exposed to elevated temperatures, e.g. about 70° C., and particularly 80° C.-150° C., or a still higher temperature, then a polymerisation reaction of methacrolein takes place. Consequently, the resulting polymer by-product may either become adhered to the walls of the reactor or clog the lines, and thereby causes serious problems in carrying out the process under large scale. This also results in a loss of the methacrolein monomer and consequently in lower production yields, which is not economically satisfactory for a large scale process.

U.S. Pat. No. 3,878,250 describes a method of preventing the polymerization of methacrolein, which consists in adding to the isolated end product methacrolein a polymerization inhibitor composition comprising at least one phosphoric acid compound and ter.butyl catechol.

U.S. Pat. No. 4,496,770 describes a process for preparing, in particular, methacrolein, wherein propanel is reacted with formaldehyde in the presence of a secondary amine and in the presence or absence of an acid. No mention is made to the problem of loss of end product by polymerisation and condensation side reactions of methacrolein.

U.S. Pat. No. 2,848,499 relates to the production of unsaturated aldehydes, such as methacrolein, by the reaction of formaldehyde and a higher aldehyde. In the example given in U.S. Pat. No. 2,848,499, it is explained that a polymerization inhibitor, such as hydroquinone, can be added to the isolated end product methacrolein.

U.S. Pat. No. 7,012,039 relates to an oxide catalyst composition, which can be used in producing methacrolein or a mixture of methacrolein and methacrylic acid. Said oxide catalyst composition exhibits not only a prolonged catalyst life, but also excellent selectivity for the desired product. No mention is made to the problem of instability of methacrolein and the resulting difficulties to conduct the process over a long period of time.

The above-mentioned processes are unsatisfactory because none of them provides a solution on how to carry out a continuous production of methacrolein without having to stop the process after only a few hours because of clogging line problems in the reaction system. The known continuous processes for preparing methacrolein can only be carried out for a few hours and have then to be stopped because methacrolein is unstable and polymerizes with ease. As a result, the production process has to be regularly stopped to remove the polymer and condensation by-products, which have either become adhered to the walls of the reactor or of the distillation column, or before clogging of the lines. This complicates drastically the continuous process for preparing methacrolein and also results in a loss of time and yield in the production.

Therefore, there still exists the need to develop a better process for preparing methacrolein on a large scale, which could be carried out continuously, with high yield and in a technically simple and efficient manner.

SUMMARY OF THE INVENTION

The purpose of the present invention is to provide a method for producing methacrolein, wherein degradation of the end product methacrolein could be prevented, thus allowing to produce continuously methacrolein on a large scale and over a long period of time.

As a result of research on how to improve the continuous process for producing methacrolein by reacting propanal with formaldehyde through a Mannich condensation reaction, the inventors have surprisingly find out that the process as described below perfectly solves the above-mentioned technical problem.

The present invention thus relates to a continuous process for preparing methacrolein by a Mannich condensation reaction of formaldehyde with propanal, characterized in that a methacrolein polymerisation inhibitor is introduced during the production process and a part thereof is recycled back into the reactor where the Mannich condensation reaction is carried out.

DETAILED DESCRIPTION OF THE INVENTION

Indeed, by introducing a methacrolein polymerization inhibitor during the production process and having a part of said polymerization inhibitor being recycled back into the reactor where the Mannich condensation reaction is carried out, it has been surprisingly observed that the formation of polymer and condensation by-products can be avoided and consequently that the process for preparing methacrolein can be carried out over a much longer period of time.

This result was not at all to be expected because the Mannich condensation reaction is carried out at elevated temperatures and the skilled person in the art would have expected that the elevated reaction temperatures would lead to inactivation of the polymerization inhibitor, or even to its chemical decomposition, resulting in clogging in the reactor where the Mannich condensation reaction is carried out. This is the reason why the previous known processes for preparing methacrolein only indicate to stabilise the isolated end product methacrolein after synthesis with a polymerization inhibitor, and in particular to avoid by-product formation during storage. In the prior art documents, no mention is made to the use of a polymerization inhibitor during the methacrolein production process.

According to the invention, the "production process system" comprises at least flow lines, a reactor, a distillation column, a reboiler, a condenser and a phase separator. A more detailed description of the production process system is given in the present application.

In a preferred embodiment of the invention, the methacrolein polymerization inhibitor is introduced into the distillation column during the production process. More preferably, it is introduced into the distillation column at an upper portion thereof.

The expression "upper portion" of the distillation column means the top of the distillation column, especially the upper third of the column.

The temperature in the upper portion of the distillation column is preferably in the range from 40 to 85° C.

According to another embodiment of the invention, the methacrolein polymerization inhibitor can also be introduced into the flow line connecting the upper portion of the distillation column and the condenser in the production process system.

According to another preferred embodiment of the invention, the methacrolein polymerization inhibitor is introduced into the flow line connecting the condenser with the phase separator in the production process system.

Preferably, the methacrolein polymerization inhibitor is introduced into the flow line connected to the entrance of the reactor in the production process system.

In another preferred embodiment, the methacrolein polymerization inhibitor is introduced into the flow line connecting the phase separator back to the distillation column.

In another preferred embodiment, the methacrolein polymerization inhibitor is introduced into the flow line connecting the lower portion of the distillation column with the entrance to the reboiler, being the exit from the reboiler connected back to the lower portion of the distillation column.

The expression "lower portion of the distillation column" means the lower third of the column.

According to a preferred embodiment of the invention, the methacrolein polymerization inhibitor is introduced into the flow line connecting the exit of the reactor with the distillation column.

Preferably, the Mannich condensation reaction is carried out in presence of a secondary amine and at least one organic acid, being the molar ratio of acid to organic base in the range from 20:1 to 1:20.

In a preferred embodiment, the Mannich condensation reaction is carried out with a residence time in the range from 0.1 to 300 seconds, specifically preferably in the range from 1 to 30 seconds. It is advantageous to use a tubular reactor as reactor at residence times below 10 minutes. The residence time here refers to the time for which the reaction mixture is reacted. All of the components are present here at reaction pressure and temperature, and said time can therefore be calculated from the distance between the mixing point and the depressurization point. The depressurization point is the point at which the mixture is brought from reaction pressure to a pressure below 5 bar.

The reaction pressure is in the range from 2 to 300 bar, preferably from 5 to 250 bar, particularly preferably from 10 to 200 bar, advantageously from 15 to 150 bar, preferably from 20 to 100 bar and in particular from 40 to 80 bar. Pressure and temperature are adjusted in such a way that the reaction always takes place below the boiling point of the reaction mixture, i.e. the reaction proceeds in the liquid phase.

The reaction temperature for the reaction of propanal with formaldehyde at the exit from the reaction zone is from 100 to 300° C., preferably from 130 to 250° C., with preference from 140 to 220° C., in particular from 150 to 210° C.

According to a preferred embodiment of the invention, the Mannich condensation reaction is carried out at a temperature of from 100 to 300° C. and at a pressure of from 5 to 100 bar.

Preferably, the concentration of methacrolein polymerization inhibitor in the reaction mixture is between 10 and 10000 ppm, preferably between 15 and 1000 ppm.

In a preferred embodiment of the invention, the methacrolein polymerization inhibitor is selected from at least one of the compounds A or B

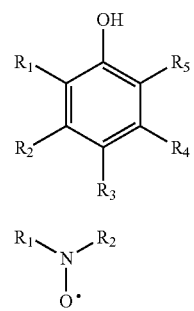

Whereby $R_1$ to $R_5$ are selected independently from each other from Alkyl, Aryl, Hydroxyl, Carboxyl or Amino. More preferably, the methacrolein polymerization inhibitor is selected from the group consisting of hydroquinones, hydroquinone ethers, such as hydroquinone monomethyl ether or di-tert-butylpyrocatechol, phenothiazine, N,N'-diphenyl-p-phenylenediamine, 4-hydroxyl-2,2,6,6-tetramethylpiperidin-1-oxyl, p-phenylenediamine, methylene blue and sterically hindered phenols, . . . , tempol, etc . . . , or a mixture thereof. Even more preferably, it is selected from hydroquinone, tempol, topanol A, hydroquinone mono methylether or a mixture thereof.

In case of using one of last mentioned methacrolein polymerization inhibitor during the methacrolein continuous process according to the invention, then the continuous process for preparing methacrolein can be combined with another reaction step, wherein the end product methacrolein is further reacted with methanol and an oxidant, preferably oxygen, in a direct oxidative esterification to give methylmethacrylate.

Further details about the Mannich condensation reaction according to the present invention are provided herein after. In particular, the reaction can be carried out with a molar ratio of propanel to formaldehyde which is preferably in the range from 2:1 to 1:2, particularly preferably from 1.5:1 to 1:1.5 and specifically preferably from 1.1:1 to 1:1.1. It is very particularly preferable to use an equimolar ratio of propanel to formaldehyde. It is thus possible, in particular at high conversions, to omit any removal and return of propanel and/or formaldehyde from the mixture obtained after the reaction.

The reaction of propanal with formaldehyde generally uses catalysts, and various systems are known here which lead to a high yield of methacrolein, with high selectivity.

The reaction of propanal with formaldehyde is carried out in the presence of acid, generally inorganic acid or organic mono-, di- or polycarboxylic acid, preferably monocarboxylic acid, in particular aliphatic monocarboxylic acid.

Carboxylic acids advantageously used are aliphatic monocarboxylic acids having from 1 to 10, preferably from 2 to 4, carbon atoms, or di- and polycarboxylic acids having from 2 to 10, preferably 2 and from 4 to 6, carbon atoms. The dicarboxylic acids and polycarboxylic acids can be aromatic, araliphatic, and preferably aliphatic, carboxylic acids. Suitable examples are acetic acid, propionic acid, methoxyacetic acid, n-butyric acid, isobutyric acid, oxalic acid, succinic acid, tartaric acid, glutaric acid, adipic acid, maleic acid, and fumaric acid. In principle, it is equally possible to use other organic acids, but they are generally less advantageous for reasons of price. Inorganic acids used are generally sulphuric acid and phosphoric acid. Acid mixtures can also be used.

It is particularly preferable to use at least one organic acid for the reaction of propanal and formaldehyde, and acetic acid is particularly preferably used here.

The proportion of acid, based on propanal, is from 0.1 to 20 mol %, advantageously from 0.5 to 10 mol %, preferably from 1 to 5 mol %.

The reaction of propanal with formaldehyde is carried out in the presence of organic bases, preferably amines, particularly preferably secondary amines. Amines that can be used are preferably those of the formula $R^1R^2NH$, where $R^1$ and $R^2$ are identical or different and are respectively an alkyl moiety having from 1 to 10, advantageously from 1 to 8, in particular from 1 to 4, carbon atoms, which can also have substitution by ether, hydroxy, or secondary or tertiary amino groups, in particular by from 1 to 2 of the said groups, or are an aralkyl moiety having from 7 to 12 carbon atoms or a cycloalkyl moiety having from 5 to 7 carbon atoms, and $R^1$ and $R^2$ can also, with the adjacent nitrogen, be members of a heterocyclic, advantageously 5- to 7-membered ring which can also comprise another nitrogen atom and/or an oxygen atom and which can have substitution by hydroxyalkyl or alkyl groups having from 1 to 4 carbon atoms.

Examples of amines that can be used are: dimethylamine, diethylamine, methylethylamine, methylpropylamine, dipropylamine, dibutylamine, diisopropylamine, diisobutylamine, methylisopropylamine, methylisobutylamine, methyl-sec-butylamine, methyl(2-methylpentyl)amine, methyl(2-ethylhexyl)amine, pyrrolidine, piperidine, morpholine, N-methylpiperazine, N-hydroxyethylpiperazine, piperazine, hexamethyleneimine, diethanolamine, methylethanolamine, methylcyclohexylamine, methylcyclopentylamine, dicyclohexylamine or appropriate mixtures.

It may also be provided that at least one of the amines used has no hydroxy group. It is particularly preferable that the proportion of amines having at least one hydroxy group is at most 50% by weight, preferably at most 30% by weight, and particularly preferably at most 10% by weight, based on the weight of the amines used.

The proportion of organic base, preferably of secondary amines, is from 0.1 to 20 mol %, advantageously from 0.5 to 10 mol %, preferably from 1 to 5 mol %, based on propanal.

The ratio of the equivalents of amine to acid is preferably selected in such a way as to give a resultant pH of from 2.5 to 9 in the reaction mixture prior to the reaction.

It can also be provided that the molar ratio of acid to organic base, preferably amine, is in the range from 20:1 to 1:20, preferably in the range from 10:1 to 1:10, particularly preferably in the range from 5:1 to 1:5 and specifically preferably in the range from 2:1 to 1:2.

The reaction mixtures can also comprise, alongside water, organic solvents, e.g. propanol, dioxane, tetrahydrofuran, and methoxyethanol.

It can also be provided that the reaction of propanel with formaldehyde to give methacrolein takes place in the presence of preferably at least 0.1% by weight, with preference at least 0.2% by weight and particularly preferably at least 0.5% by weight, of methanol, based on formalin.

According to one particular embodiment, formaldehyde and propanel can be mixed before the said starting materials are brought to reaction pressure and/or temperature.

DETAILED DESCRIPTION OF THE INVENTION

In one preferred embodiment, a mixture (advantageously equimolar mixture) of formaldehyde and propanel can be heated by way of a heat exchanger to the desired reaction temperature and passed into a tubular reactor. A catalyst solution (solution of the secondary amine and of an acid, advantageously in $H_2O$) optionally heated by way of a heat exchanger likewise to the reaction temperature can be injected at the reactor inlet into the said mixture. The strongly exothermic reaction begins, and the temperature of the reaction mixture increases further. It is preferable that a pressure-retention valve at the reactor outlet is used to keep the pressure under which the reaction proceeds at values such that the reaction mixture still remains liquid during the reaction time, even when temperatures in the reactor are high. After the reaction, the reaction mixture can be depressurized to atmospheric pressure and worked up. In the production of methacrolein from propanel and formaldehyde it is preferable that the reaction mixture is passed into a column for steam-stripping. The methacrolein is discharged together with water at the top of the column. The mixture is condensed and separated by way of a phase separator to give an upper and a lower phase. The upper phase comprises the methacrolein. The lower phase is composed mainly of water. It can preferably in turn be at least to some extent returned to the column in order to remove the residual methacrolein dissolved therein.

The aqueous catalyst solution can be drawn off at the bottom of the column together with the water formed in the reaction and the water of the formaldehyde solution. For the purposes of further processing, the liquid from the bottom of the column can be discarded if very little amine and/or acid is used and return of the catalyst is therefore then not worthwhile.

However, in the case of higher concentrations of amine and/or of acid in the material discharged at the bottom of the column it is also possible to carry out distillative removal of water at least to some extent and in turn to return the catalyst solution to the reactor. Another possibility is to divide the material discharged at the bottom of the column into two sub-streams in such a way that one sub-stream comprises precisely the amount of water that was formed during the reaction and introduced with the starting materials. The said sub-stream is then removed from the system, and the remaining proportion is returned to the reactor. Aqueous formaldehyde and propanel can also be separately preheated and introduced into the reactor.

According to the invention, the methacrolein can be further reacted with methanol and an oxidant, preferably oxygen, in a direct oxidative esterification reaction to give methylmethacrylate.

For the purposes of the present invention, a direct oxidative esterification reaction is a process in which methacrolein is reacted directly, i.e. without formation of large amounts of methacrylic acid, to give methylmethacrylate in the presence of methanol and of an oxidant, preferably oxygen.

The suitable distillation temperature in the distillation column preferably used in the described process for work-up of the reaction mixture obtained from the oxidative esterification varies as a function of the distillation pressure, of the composition of the liquid in the distillation tower, of the number of plates in the distillation tower and the like. However, in order to minimize the formation of polymerization by-products and the formation of high-boiling-point compounds which represent a yield loss, based on methacrolein, it is preferable that the distillation temperature is minimized. Nevertheless, if a very low distillation temperature is selected, disadvantages can arise. Among these are, by way of example, that a low distillation pressure also has to be selected. This can require the use of a disadvantageously large distillation column. Moreover it can be necessary to use a coolant for concentrating the gas phase in the uppermost portion of the distillation tower. It is preferable that the distillation temperature, or the temperature of the liquid in the column, is in the range from 20 to 100° C., particularly from 40 to 85° C. The distillation pressure is calculated from the said temperature.

Methacrolein polymerization inhibitors are well known to persons skilled in the art, examples being hydroquinones, hydroquinone ethers, such as hydroquinone monomethyl ether or di-tert-butylpyrocatechol, phenothiazine, N,N'-diphenyl-p-phenylenediamine, 4-hydroxy-2,2,6,6-tetramethylpiperidin-1-oxyl, p-phenylenediamine, methylene blue and sterically hindered phenols. The said compounds can be used individually or in the form of mixtures and are generally available commercially. The action of the stabilizers mostly consists in their action as free-radical scavengers for the free radicals arising during polymerization. Reference is made to the familiar technical literature for further details, in particular to Rompp-Lexikon Chemie [Römpp's Chemical Encyclopaedia]; Editors: J. Falbe, M. Regitz; Stuttgart, New York; 10th Edition (1996); keyword "Antioxidantien" [Antioxidants] and to the references cited therein.

In particular, phenols are preferably used as polymerization inhibitor. Particularly surprising advantages can be achieved when hydroquinone monomethyl ether is used. The proportion of the inhibitors, individually or in the form of a mixture, can generally be from 0.001 to 0.5% by weight, based on the weight of the entire composition.

EXAMPLES

The examples below serve for further explanation of preferred embodiments of the present invention, but are not intended to restrict the invention.

Example 1

Column K350 as described below was used to distillate crude Methacrolein. It was equipped with 5,3 m Rombopack 12M with a diameter of 100 mm. Feed is directed to the top of the distillation column. Condensor WT351 was operated with cooling water (500 l/h) and the subsequent offgas condenser WT354 with 2° C. brine. The column is operated at ambient pressure. The combined distillate is cooled in cooler WT353 with 2° C. brine and sent to the horizontal phase separator B351. B351 has 60 cm separation length with 2×16 cm Sulzer CY packing elements. The upper phase overflows to the MAL storage vessel B353. Using P351 with a maximum flowrate of 9 l/min, the lower phase is pumped back to the column as reflux and controls the interface level of B351. The sump of K350 is pumped with P352 at 1500 l/h to a falling film reboiler with 0,12 m2 area operated with 11 barg steam and the control valve of the steam being 100% open. The bottom take-out is directed from the discharge of pump P352 to storage vessel B355 and controls the level in the sump of the distillation column K350.

An inhibitor solution of 1 wt % Tempol in water can be pumped from feed vessel B354 to the top of condenser WT351 using pump P354 (Knauer HPLC pump K-501) at a flowrate of 30 g/h.

The feed to the distillation column is provided by the outlet of reactor R55. Propionaldehyde (6.45 kg/h), Formalin (9.00 kg/h, 55 gew % water), dimethylamine (312 g/h), acetic acid (183 g/h) and a recycle from the bottom of the distillation column (9.50 kg/h) are sent to the reactor. The reactor is operated between 160° C. and 180° C. at 30 bar. The temperature at the top of the distillation column was 64° C. and in the bottom of the distillation column 100° C.

Propionaldehyde conversion was xx-xx % and selectivity of Propionaldehyde to MAL was zz-zz %.

While the inhibitor solution was pumped to the phase separator, no polymer was visible in the distillation column during a production campaign of 10 days.

Comparative Example 1

The setup as described in Example 1 was operated without feeding inhibitor solution. Polymer was observed in the distillation column after 8 hours of operation.

Example 2

Column K1 as described below was used to distillate crude Methacrolein. It was equipped with 0,7 m of Sulzer EX packing with a diameter of 50 mm. Feed is directed to the top of the distillation column. Condensor WT5 was operated with cooling water and the subsequent offgas condenser WT6 with 2° C. brine. The column is operated at ambient pressure. The combined distillate is sent to the horizontal phase separator B4. The upper phase of the phase separator is pumped to the MAL storage vessel B5 controlling the total level in the phase separator. The lower phase is pumped back to the column as reflux and controls the interface level of B4. Heat is provided to the column using an electric heater with a maximum duty of 300 W, controlling the column temperature TIRC7 (located at 20 cm of packing measured from the top of the column) around 75° C. The bottom take-out of K1 is pumped to storage vessel B7 controlling the liquid level in the sump of the distillation column K1.

An inhibitor solution of 0.2 wt % Tempol in water can be pumped from feed vessel B3 to the feed of the phase separator B4 using pump P3 (Knauer HPLC pump K-501) at a flowrate of 23.5 g/h.

The feed to the distillation column is provided by the outlet of a reactor. A Propionaldehyde/Formalin solution (607.2 g/h), a catalyst solution (23 g/h) and a recycle from the bottom of the distillation column (334 g/h) are sent to the reactor. The reactor is operated at 180° C. at 30 bar with a residence time of 10 s. The Propionaldehyde/Formalin solution had a concentration of xxwt % Propionaldehyde, yy wt % Formaldehyde, yy wt % Methanol and zz wt % water. The catalyst solution had a concentration of xx wt % Dimethylamine and yy wt % acetic acid. The reactor outlet is quenched to 20° C. prior to entering the distillation column.

The temperature at the top of the distillation column was 64° C. and in the bottom of the distillation column 100° C.

Propionaldehyde conversion was xx % and selectivity of Propionaldehyde to MAL was zz %.

While the inhibitor solution was pumped to the phase separator, no polymer was visible in the distillation column after 210 h of operation.

Comparative Example 2

The setup as described in Example 2 was operated without feeding inhibitor solution. Polymer was observed in the distillation column after 6 hours of operation.

The invention claimed is:

1. A continuous process for preparing methacrolein by a Mannich condensation reaction of formaldehyde with propanal, said comprising:
   introducing a methacrolein polymerization inhibitor into a production process system, and
   recycling a part of said methacrolein polymerization inhibitor back into a reactor where the Mannich condensation reaction is carried out,
   said production process system comprising flow lines, a reactor, a distillation column, a reboiler, a condenser, and a phase separator,
   wherein the methacrolein polymerization inhibitor is introduced into the distillation column in the production process system.

2. The continuous process for preparing methacrolein according to claim 1, wherein the methacrolein polymerization inhibitor is introduced into the distillation column at an upper portion thereof.

3. The continuous process for preparing methacrolein according to claim 2, wherein a temperature at the upper portion of the distillation column is in the range from 40 to 85° C.

4. The continuous process for preparing methacrolein according to claim 1, wherein the methacrolein polymerization inhibitor is introduced into a flow line connecting an upper portion of the distillation column and the condenser in the production process system.

5. The continuous process for preparing methacrolein according to claim 1, wherein the methacrolein polymerization inhibitor is introduced into a flow line connecting the condenser with the phase separator in the production process system.

6. The continuous process for preparing methacrolein according to claim 1, wherein the methacrolein polymerization inhibitor is introduced into a flow line connected to an entrance of the reactor in the production process system.

7. The continuous process for preparing methacrolein according to claim 1, wherein the methacrolein polymerization inhibitor is introduced into a flow line connecting the phase separator back to the distillation column.

8. The continuous process for preparing methacrolein according to claim 1, wherein the methacrolein polymerization inhibitor is introduced into a flow line connecting a lower portion of the distillation column with an entrance to the reboiler, wherein an exit from the reboiler is connected back to the lower portion of the distillation column.

9. The continuous process for preparing methacrolein according to claim 1, wherein the methacrolein polymerization inhibitor is introduced into a flow line connecting an exit of the reactor with the distillation column.

10. The continuous process for preparing methacrolein according to claim 1, wherein the Munich condensation reaction is carried out in presence of a secondary amine and at least one organic acid, wherein a molar ratio of acid to organic base is in the range from 20:1 to 1:20.

11. The continuous process according to claim 1, wherein the Mannich condensation reaction is carried out with a residence time in the range from 0.1 to 300 seconds.

12. The continuous process according to claim 1, wherein the Mannich condensation reaction is carried out at a temperature of from 100 to 300° C.' and at a pressure of from 5 to 100 bar.

13. The continuous process according to claim 1, wherein a concentration of the methacrolein polymerization inhibitor in a reaction mixture is between 10 and 10,000 ppm.

14. The continuous process according to claim 1, wherein the methacrolein polymerization inhibitor is selected from at least one of the compounds A or B

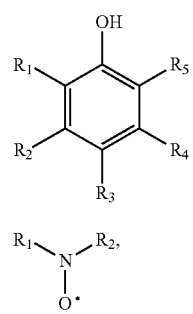

with $R_1$ to $R_5$ selected independently from each other, from alkyl, hydroxyl, carboxyl, or amino.

15. The continuous process according to claim 14, wherein the methacrolein polymerization inhibitor is selected from the group consisting of hydroquinones, hydroquinone ethers, phenothiazine, diphenyl-p-phenylenediamine, 4-hydroxyl-2,2,6,6-tetramethylpiperidin-1-oxyl, p-phenylenediamine, methylene blue, sterically hindered phenols, tempol, EDTA, and a mixture thereof.

16. The continuous process according to claim 15, wherein the methacrolein polymerization inhibitor is hydroquinone, tempol, topanol A, hydroquinone mono methylether, or a mixture thereof.

17. The continuous process according to claim 16, wherein the methacrolein is further reacted with oxygen and methanol in a direct oxidative esterification to give methylmethacrylate.

* * * * *